(12) United States Patent
Sasaki et al.

(10) Patent No.: US 6,337,322 B1
(45) Date of Patent: Jan. 8, 2002

(54) PREVENTIVES AND REMEDIES FOR INTESTINAL MUCOSAL DISORDER

(75) Inventors: Hajime Sasaki; Kenji Mizumoto; Hisae Kume, all of Odawara (JP)

(73) Assignee: Meiji Milk Products Co., Ltd., Tokyo (JP)

( * ) Notice: Subject to any disclaimer, the term of this patent is extended or adjusted under 35 U.S.C. 154(b) by 0 days.

(21) Appl. No.: 09/600,867

(22) PCT Filed: Feb. 5, 1999

(86) PCT No.: PCT/JP99/00501

§ 371 Date: Oct. 2, 2000

§ 102(e) Date: Oct. 2, 2000

(87) PCT Pub. No.: WO99/39703

PCT Pub. Date: Aug. 12, 1999

(30) Foreign Application Priority Data

Feb. 9, 1998 (JP) ............................................ 10-040994

(51) Int. Cl.[7] ........................ A61K 31/66; A61K 31/13; A61K 38/00
(52) U.S. Cl. ........................ 514/114; 514/669; 514/12; 514/2
(58) Field of Search .............................. 514/114, 669, 514/12, 2

(56) References Cited

FOREIGN PATENT DOCUMENTS

JP          8-310944          11/1996

OTHER PUBLICATIONS

R. Rao, et al., European Journal of Pharmacology, vol. 303, No. 3, pp. 209 to 212, "Epidermal Growth Factor Protects Mouse Ileal Mucosa from Triton X–100–Induced Injury", 1996.

M. Sottili, et al., Gastroenterology, vol. 109, No. 1, pp. 24 to 31, "Up–Regulation of Transforming Growth Factor α Binding Sites in Experimental Rabbit Colitis", 1995.

"Changes in activity of alkaline and acid phosphatases in stomach mucous membranes and samll intestines under action of amino alcohols", Mnatsakanyan et al, 1966, Bio. Zh. Arm.: Abstract.*

"Ethanolamine modulation of phospholipid metabolite levels in human B–cell malignancies", Shedd et al, 1995, Proc Annu Meet Am Assoc Cancer Res: Abstract.*

* cited by examiner

Primary Examiner—Marianne C. Seidel
Assistant Examiner—Brian-Yong Kwon
(74) Attorney, Agent, or Firm—Oblon, Spivak, McClelland, Maier & Neustadt, P.C.

(57) ABSTRACT

Preventives and remedies for intestinal mucosal disorders and diseases caused thereby which contain as the active ingredient a member selected from the group consisting of ethanolamine, phosphoethanolamine, phosphoglycerolethanolamine and salts thereof. These preventives and remedies inhibit shrinkage of the intestinal mucosa and have a beneficial effect on various functions of the intestinal tract.

12 Claims, 5 Drawing Sheets

PREVENTIVES AND REMEDIES FOR INTESTINAL MUCOSAL DISORDER

TECHNICAL FIELD

The present invention relates to a drug for preventing and treating intestinal mucosal disorders.

BACKGROUND ART

Currently, pervenous nutrition and enteral nutrition are the predominant therapeutic methods used in the field of gastrointestinal surgery, and greatly contribute to therapeutic outcomes. However, these two methods have drawbacks. Pervenous nutrition and enteral nutrition are employed as a trophotherapy to treat invasion precipitated by surgery or grave infectious diseases; malignant tumors; chronic marasmic conditions; hepatic cirrhosis; chronic obstructive lung diseases; or similar conditions. Problems reported in relation to pervenous nutrition (introduction of hyperalimentation by transfusion via the central vein) include atrophy of the intestinal tract mucosa (Johnson, L. R. et al.: Gastroenterology. 68: 1177–1183, 1975), disturbance of intestinal flora (Winitz, M. et al.: Am. J. Nutrition. 23: 546–559, 1970), decrease in intestinal absorption (King, A. B.: Ed. Bounous, G. CRC Press, Florida, 1993), and a deterioration in the biological protection mechanism provided by intestinal tract barrier immunity (Alverdy, J. C.: Ed. Bounous, G. CRC Press, Florida, 1993). When enteral nutrition through the intestinal tract—which resembles peroral ingestion more closely than pervenous nutrition does—is carried out, aggravation of mucosal lesions and diarrhea can cause a reduction in the absorption of calorific elements and nutritional substances, thereby possibly exacerbating the conditions. For example, when enteral elemental nutrition of low residue content is administered over a long term, atrophy of the small intestine, reduced nutritional absorption, and diarrhea are possibly induced by the administration of a hyperosmolar solution.

Thus, there is demand for a preventive and therapeutic agent to treat disorders of the intestinal mucosa. Thus far, there have been known a drug for preventing atrophy of the intestinal mucosa (Japanese Patent Application Laid-Open (kokai) No. 5-9121) and a drug for preventing and treating disorders of the intestinal mucosa, which drug contains M-CSF as an active ingredient (Japanese Patent Application Laid-Open (kokai) No. 6-321801).

In addition, organic acids such as butyric acid and propionic acid are known to promote proliferation (Sakata, T.: British Journal of Nutrition. 58: 95–103, 1987) and assist the metabolism of epithelial cells in the intestinal tract (Scheppach, W.: Gut. 35: S35–S38, 1994). Amino acids such as glutamine are also known to promote proliferation and assist the metabolism of cells in the intestinal tract (Fox, A. D. et al.: J. Parenteral and Enteral Nutrition. 12: 325–331, 1988; Klimberg, V. S. et al.: Arch. Surg. 125: 1040–1045, 1990; Odweyer, S. T. et al.: J. Parenteral and Enteral Nutrition. 13: 579–585, 1989).

However, these drugs used in preventing and treating intestinal mucosal disorders are unsatisfactory with regard to effectiveness and dose.

Thus, an object of the present invention is to provide a substance effective in preventing and treating intestinal mucosal disorders which are caused by a variety of tissue disorder factors, inter alia, long-term administration of pervenous or enteral nutrition.

DISCLOSURE OF THE INVENTION

The present inventors have conducted careful research into substances effective in preventing and treating intestinal mucosal disorders, and have found that ethanolamine, phosphoethanolamine, phosphoglycerolethanolamine, or a salt thereof (hereinafter these compounds may be collectively referred to as "ethanolamines")—contained in organisms and being safe—are effective in preventing and treating intestinal mucosal disorders. The present invention has been accomplished on the basis of this finding.

Accordingly, the present invention provides a drug for preventing and treating intestinal mucosal disorders or pathological conditions caused by the disorders, which drug contains as an active ingredient a member selected from the group consisting of ethanolamine, phosphoethanolamine, phosphoglycerolethanolamine, and salts thereof.

The present invention also provides use of a member selected from the group consisting of ethanolamine, phosphoethanolamine, phosphoglycerolethanolamine, and salts thereof in the manufacture of a drug for preventing and treating intestinal mucosal disorders or pathological conditions caused by the disorders.

Furthermore, the present invention provides a method for treating intestinal mucosal disorders or pathological conditions caused by the disorders, which method comprises administering to a patient in need thereof an effective amount of a member selected from the group consisting of ethanolamine, phosphoethanolamine, phosphoglycerolethanolamine, and salts thereof.

BEST MODES FOR CARRYING OUT THE INVENTION

Figure 1:
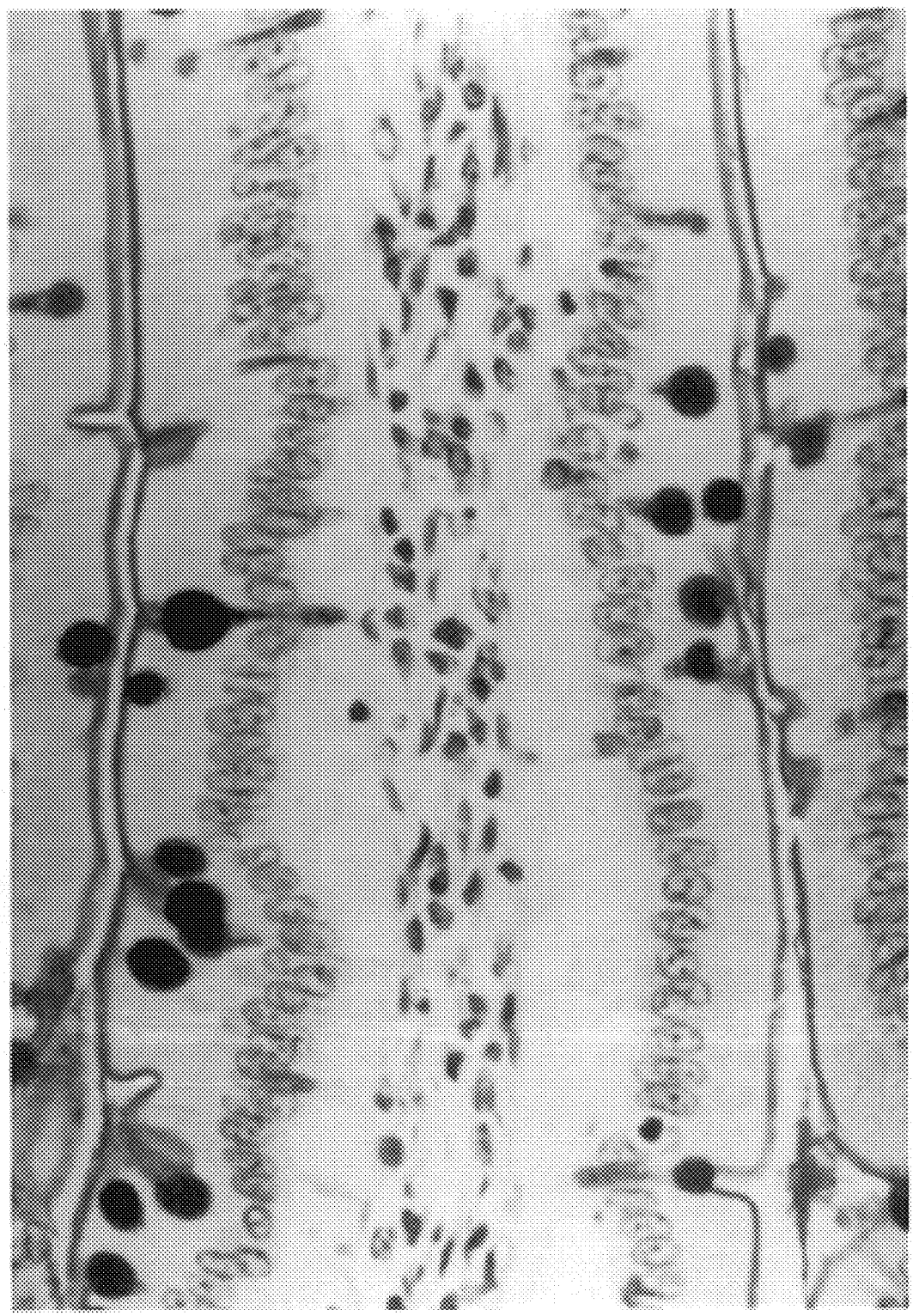
FIG. 1 is a microscopic photograph of a section of duodenal villous tissue taken from a rat in the solid feed ingestion group in Test Example 1, the tissue section having been subjected to PAS staining (magnification: ×330).

Ethanolamine, phosphoethanolamine, and phosphoglycerolethanolamine which are active ingredients of a drug of the present invention for preventing and treating intestinal mucosal disorders can be widely found in nature. These compounds are known to be biologically essential components as signal-transmitter substances, and these compounds have similar physiological activity.

These compounds may form salts with acids such as hydrochloric acid, sulfuric acid, nitric acid, and phosphoric acid, the present invention also encompassing these salts. Of these, hydrochloric acid salts are preferred.

In the present invention, the term "intestinal mucosal disorder" encompasses one induced by a variety of tissue disorder factors. For example, atrophy or regression of intestinal mucosa that may be induced by a damaging substance such as a drug or alcohol; long-term administration of component nutrition or a hyperosmolar solution; or oxygen stress.

Accordingly, the drug for preventing and treating intestinal mucosal disorders is also effective in preventing and ameliorating conditions caused by such intestinal mucosal disorders; e.g., compromised function of the intestinal tract such as reduced absorption or diarrhea (Odweyer, S. T. et al.: 579–585, 1989; Grant, J. P. and Synder P. J.: J Drug. Res. 44: 506–513, 1988; Hosoda, N. et al.: J. Surg. Res. 47: 129–133, 1989); compromised intestinal tract barrier function and immunity of the intestinal tract caused by atrophy of the mucosal tissue of the intestinal tract; and food allergy induced by a food-derived antigen which invades due to the decreased immunity.

Generally, in epithelial tissue of the intestinal tract, crypt cells contained in sub-microvillus portions actively divide, thereby providing new cells to the microvilli. The cells are transferred to the tip portion of each microvillus, and replace old deciduous cells, thereby renewing all the microvilli. Such division of intestinal epithelial cells is thought to be promoted by a cell growth factor (Booth, C. et al.: In Vitro Cell. Dev. Biol. 31: 234–243, 1995). When rats are fasted, atrophy of epithelial mucosal tissue of the intestinal tract is induced (McManus, J. and Isselbacher, K.J.: Gastroenterology. 59: 214–221, 1970, Goodlad, R. A. et al: Clinical Science. 74: 301–306, 1988). However, the development of atrophy is suppressed by enterally administering EGF—a cell growth factor which promotes proliferation of epithelial cells. Promotion of cell division and hyperenergia in cell functions, which are induced by stimulating epithelia cells with an EGF, are thought to suppress atrophy of epithelial mucosal tissue (Ulshen, M. H. and Raasch, R. H.: Clinical Science. 90: 427–431, 1996).

When only ethanolamine is added to primarily cultured liver cells, proliferation-promoting activity is not observed, whereas when ethanolamine is added in the presence of a cell growth factor such as EGF, proliferation of liver cells is synergistically promoted by ethanloamine present at a concentration of 10-100 $\mu$M (Japanese Patent Application Laid-Open (kokai) No. 8-310944). Thus, ethanolamine is considered to potentiate the action of a cell growth factor. From another perspective, ethanolamine is known to promote proliferation of epithelial cells such as keratinocyte tsao, M. C. et al.: J. Cell Physiol, 110; 219–229, 1982).

Thus, the effect of suppressing intestinal mucosal disorders provided by ethanolamine, phosphoethanolamine, phosphoglycerolethanolamine, and salts thereof according to the present invention is believed to be provided through the following mechanism. Specifically, these ethanolamines promote proliferation of epithelial cells in the intestinal tract that are stimulated by a cell growth factor such as EGF, thereby potentiating the functions of epithelial cells in the intestinal tract.

Toxicity of these ethanolamines is not proven from acute toxicity test results (Japanese Patent Application Laid-Open (kokai) No. 9-224605). Since ethanolamines have a low-molecular weight, absorbability thereof may be high when they are administered perorally.

Thus, the drug of the present invent ion for preventing and treating intestinal mucosal disorders may be prepared by forming, into a pharmaceutical composition of any of variety of forms, a pharmacologically effective amount of any ethanolamine in combination with a pharmaceutically acceptable, conventional non-toxic carrier. Examples of dosage forms include peroral forms such as powders, granules, sugarcoated tablets, capsules, and ampoules; subcutaneous, intramuscular, or intravenous injections; and suppositories. Although the dose of the drug varies in accordance with symptoms and administration route, the drug is typically administered to an adult at a dose of 10–5000 mg/day, preferably 50–2000 mg/day, divided into 3 or 4 separate doses. In terms of the form of administration, it is particularly preferred that the drug be added to an enteral nutrition agent. In this case, the proportion of the drug added is 10–800 $\mu$g based on 1 kcal of enteral nutrition, preferably 100–500 $\mu$g. Ingestion of 1500 kcal of enteral nutrition corresponds to 150–750 mg of ethanolamines, which may be sufficiently effective in preventing and treating intestinal mucosal disorders.

The drug of the present invention for preventing and treating intestinal mucosal disorders may be employed in combination with a cell growth factor such as EGF or FGF due to the drug's mechanism of action. The cell growth factor may be of a naturally occurring type or produced through genetic engineering in a recombinated form. In addition, derivatives thereof exhibiting a similar activity may also be employed.

As described hereinabove, the drug of the present invention for preventing and treating intestinal mucosal disorders prevents intestinal mucosal disorders induced by a variety of tissue disorder factors, inter alia, atrophy of intestinal mucosa caused by the long-term administration of pervenous or enteral nutrition. In addition, employment of the drug can prevent reduced nutritional absorption and diarrhea induced by atrophy, lowering of barrier functions and immunity of the intestinal tract, and food allergies. The drug is also effective in the regulation of intestinal flora.

EXAMPLES

The present invention will next be described in more detail by way of test examples.

Test Example 1

Six-week-old male Sprague-Dawley rats (purchased from Nippon Charles River) were employed in the test. Water and solid feed (CRF-1, product of Oriental Yeast) were freely ingested by the rats. After one-week of preliminary breeding, as shown in Table 1, the rats were divided into the following six groups (three rats per group): a group made up of rats to which solid feed was given (hereinafter this group will be referred to as the "solid feed ingestion group"); a group made up of fasting rats to which only water was given (hereinafter this group will be referred to as the "water ingestion fasting group"); and four other groups made up of fasting rats to which only aqueous solutions containing ethanolamine hydrochloride (Etn) (product of Sigma) of different concentrations (1, 10, 100, and 1000 $\mu$M) were given (hereinafter each of these groups will be referred to as an "ethanolamine hydrochloride ingestion fasting group").

The test was carried out for 48 hours. For the fasting groups, solid feed was removed in the morning of the day on which the test was initiated. During the 48 hours, solid feed, water, and an ethanolamine hydrochloride-containing aqueous solution were freely ingested by the rats in the solid feed ingestion group, the water ingestion fasting group, and the ethanolamine hydrochloride ingestion fasting group, respectively. The amount of water ingested during the 48 hours was measured, and the amount of ingested ethanolamine per rat was calculated on the basis of the amount of water (Table 2).

For each group, the rats were weighed at the time of test initiation and the time of test completion, in order to obtain the average weight (Table 1). In the fasting groups, any changes in the weight of the rats that could be attributed to ethanolamine ingestion were not observed.

TABLE 1

| Group | Feed | Concentration of Etn in water ($\mu$M) | Weight ± standard deviation (g) | |
|---|---|---|---|---|
| | | | Initial | Final |
| 1 | Fasting | 0 | 235.9 ± 4.0 | 208.9 ± 3.7 |
| 2 | Fasting | 1 | 235.6 ± 4.0 | 208.2 ± 3.1 |
| 3 | Fasting | 10 | 239.5 ± 7.5 | 209.4 ± 7.4 |
| 4 | Fasting | 100 | 238.8 ± 5.7 | 210.4 ± 3.9 |
| 5 | Fasting | 1000 | 240.2 ± 7.9 | 213.1 ± 6.7 |
| Solid feed ingestion group | | 0 | 239.1 ± 5.0 | 272.2 ± 6.1 |

Figure 2:
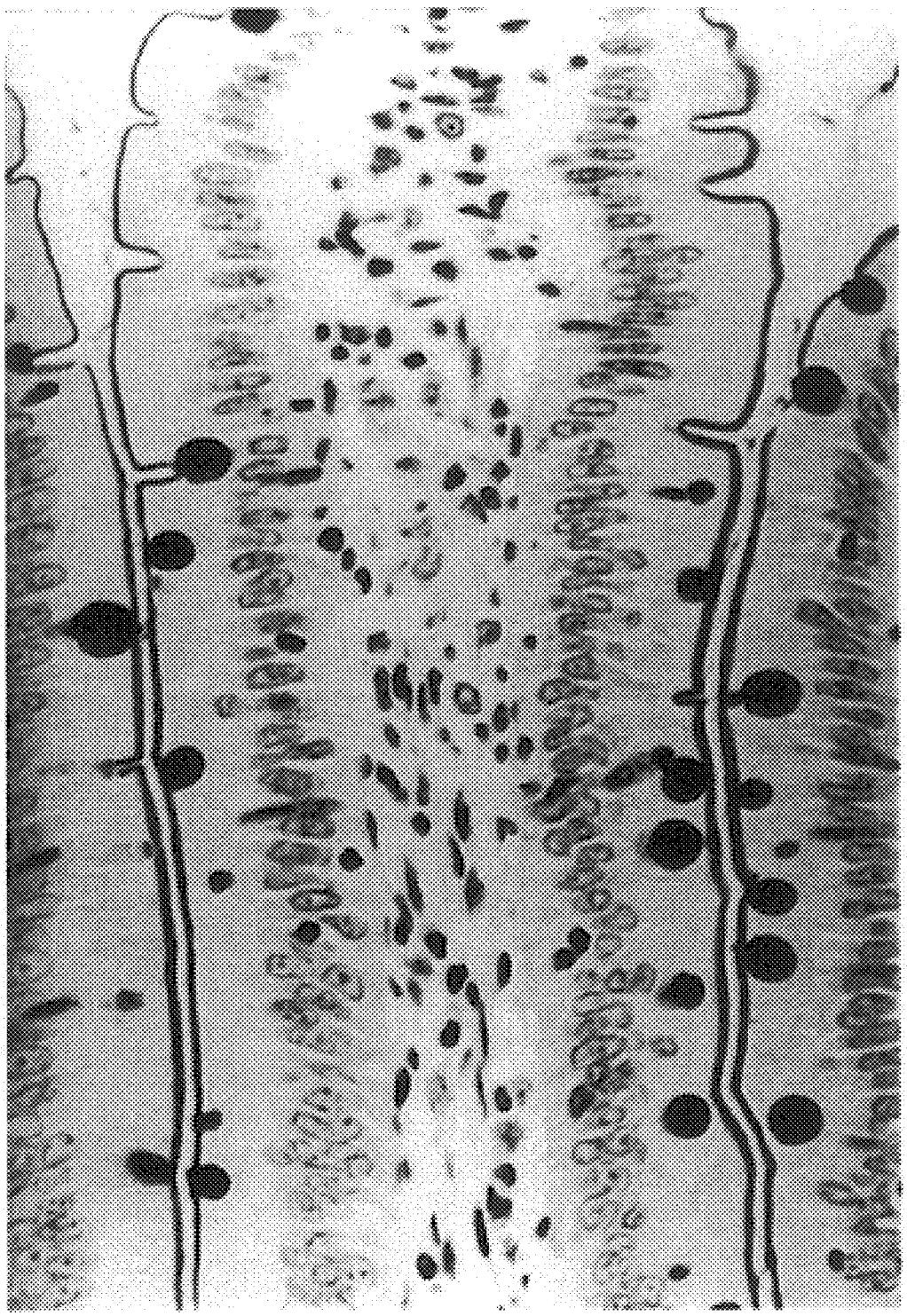
FIG. 2 is a microscopic photograph of a section of duodenal villous tissue taken from a rat in the water ingestion fasting group in Test Example 1, the tissue section having been subjected to PAS staining (magnification: ×330).
Figure 3:
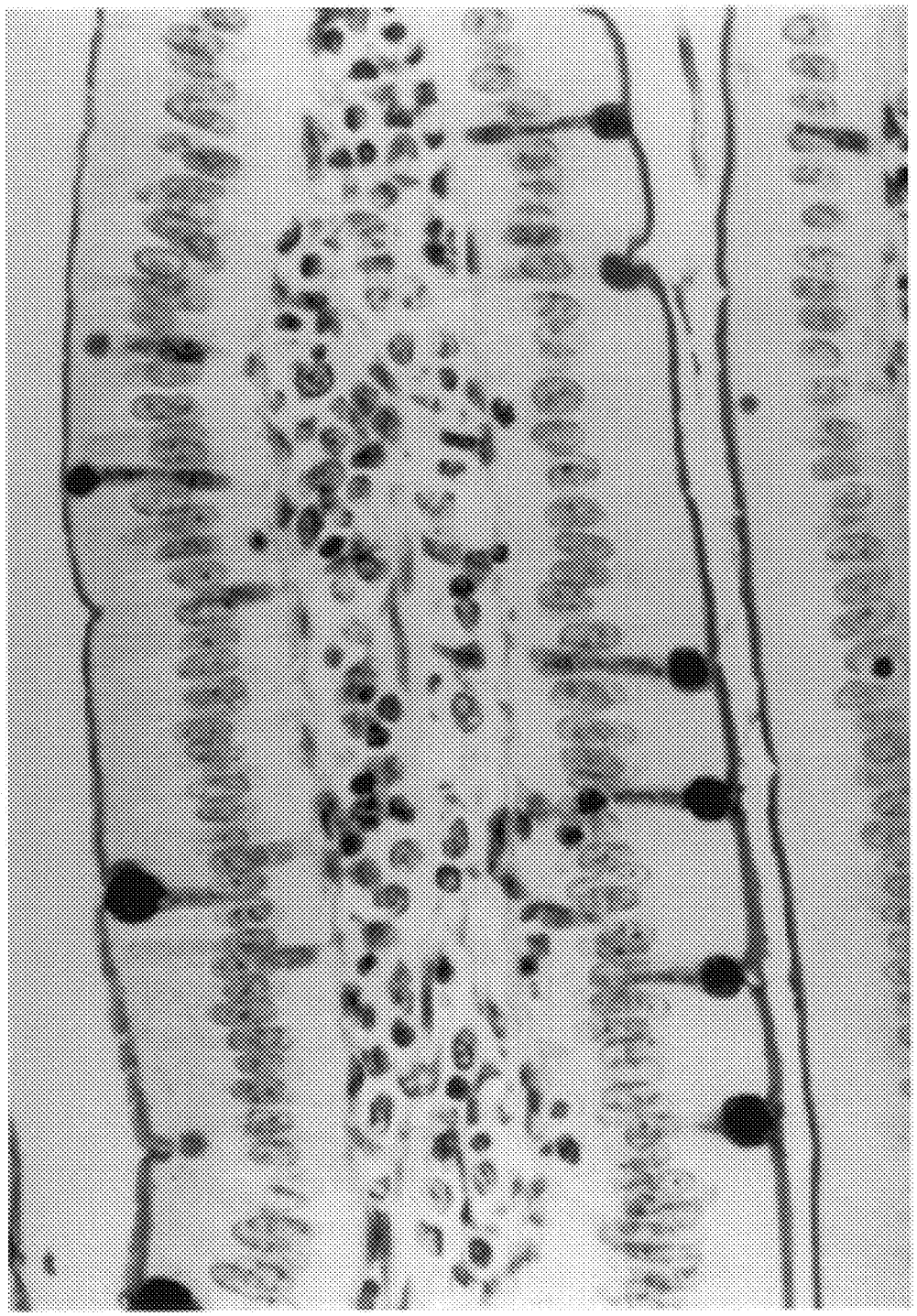
FIG. 3 is a microscopic photograph of a section of duodenal villous tissue taken from a rat in the ethanolamine hydrochloride (100 $\mu$m)-containing aqueous solution ingestion fasting group in Test Example 1, the tissue section having been subjected to PAS staining (magnification: ×330).

After completion of the 48-hour test, the rats from each group were anesthetized with ether, and whole blood was collected from each rat through the inferior vena cava. The small intestine was excised from each rat, and a duodenal portion (size: 1 cm in length) was removed from a position 5 cm in the direction of the anus away from the pylorus. The removed portion was fixed in phosphate buffered formalin. After 24-hour fixation, the duodenal portion was embedded in paraffin using a conventional technique, to thereby prepare a tissue section. The thus-prepared tissue sample was subjected to PAS staining, and then observed. The results are shown in FIGS. 1 to 3.

Table 2 shows the effect of ethanolamine hydrochloride on the atrophication of the duodenal epithelial mucosa tissue, which is caused by fasting.

TABLE 2

| | | Observation items | | | |
|---|---|---|---|---|---|
| Concentration of Etn in water ($\mu$M) | Ingestion amount $\mu$g/kg/day | Size of cell | Intercellular space | Size of nucleus | Density of secretion granules |
| 0 | — | Small | Large | Small | Low |
| 1 | 6 | Small | Large | Small | Low |
| 10 | 34 | Small | Large | Small | Low |
| 100 | 330 | Large | None | Large | High |
| 1000 | 4500 | Large | None | Large | High |
| Solid feed ingestion group | | Middle to Large | None | Middle to Large | High |

The following is apparent from Tables 1 and 2 and FIGS. 1 to 3.

In the rats of the water ingestion fasting group and the rats of the ethanolamine hydrochloride (1 or 10 $\mu$M) ingestion fasting groups, an increase in the intercellular space due to shrinkage of cells and atrophy of epithelial mucosa cells were observed, as compared with the rats in the solid feed ingestion group (Table 2 and FIGS. 1 and 2). In addition, in the rats of these fasting groups, the cell nuclei were reduced in size and did not stably maintain their normal position within the cell (Table 2 and FIGS. 1 and 2). In contrast, in the rats of the ethanolamine hydrochloride (100 1$\mu$M) ingestion fasting group, enlarged intercellular spaces and cell atrophy were not observed, as compared with the rats of the solid feed ingestion group (Table 2 and FIG. 3). In the rats of the ethanolamine hydrochloride (100 $\mu$M) ingestion fasting group, the cell nuclei were considerably enlarged, as compared with the rats of the water ingestion fasting group and the ethanolamine hydrochloride (1 or 10 $\mu$M) ingestion fasting group. In addition, in the rats of the ethanolamine hydrochloride (100 $\mu$M) ingestion fasting group, the nuclei were situated centrally in respective cells, the position remaining constant (Table 2 and FIG. 3).

In the rats of the solid feed ingestion group and the ethanolamine hydrochloride (100 $\mu$M) ingestion fasting group, mucus-secreting granules in goblet cells, which granules secrete a mucous substance, were heavily stained; i.e., a PAS positive substance in the granules was heavily stained through the PAS staining, as compared with the rats of the water ingestion fasting group. In addition, in the rats of the solid feed ingestion group and the rats of the ethanolamine hydrochloride (100 $\mu$M) ingestion fasting group, the structure of a PAS positive substance in the granules, which was strongly stained, was observed (FIGS. 1 and 3).

As is apparent from the above results, ethanolamine hydrochloride is effective for the prevention and treatment of atrophy of the small intestine caused by fasting.

Test Example 2

Nine-week-old CD (SD) IGS male rats were employed in the test. The rats were kept in individual fasting cages, and the day after initiation of fasting was regarded as the first fasting day. Fasting (i.e., provision of no food and no water) was carried out for four days, and on the fourth day the rats were sacrificed through exsanguination. A 5% dextrose solution was intraperitoneally administered to each rat in an amount of 10 mL on the basis of body weight (100 g) from the first fasting day to the third fasting day, to thereby induce disorders.

The rats were divided into two groups: a control group and a drug administration group. To the rats of the control group, sterile water was orally administered in an amount of 0.5 mL per 100 g of body weight twice a day, at 10:00 AM and 4:00 PM. To the rats of the drug administration group, ethanolamine hydrochloride was administered in an amount of 250 mg/5 mL/kg twice a day, at 10:00 AM and 4:00 PM. The administration was carried out from the first fasting day to the third fasting day. On the fourth fasting day, the rats were sacrificed through cervical dislocation, and the stomach and the duodenum were removed from each rat. The inside of the intestinal tract was washed with saline. Subsequently, the pylorus was ligated and the tract was also ligated at a position 4 cm from the pylorus. A 10% buffered formalin solution (2 mL) was injected into the intestinal tract, and the entire intestinal tract was fixed in 10% buffered formalin solution. After fixation, a tissue section was prepared using a conventional technique, and the resultant tissue section was subjected to HE staining.

Figure 4:
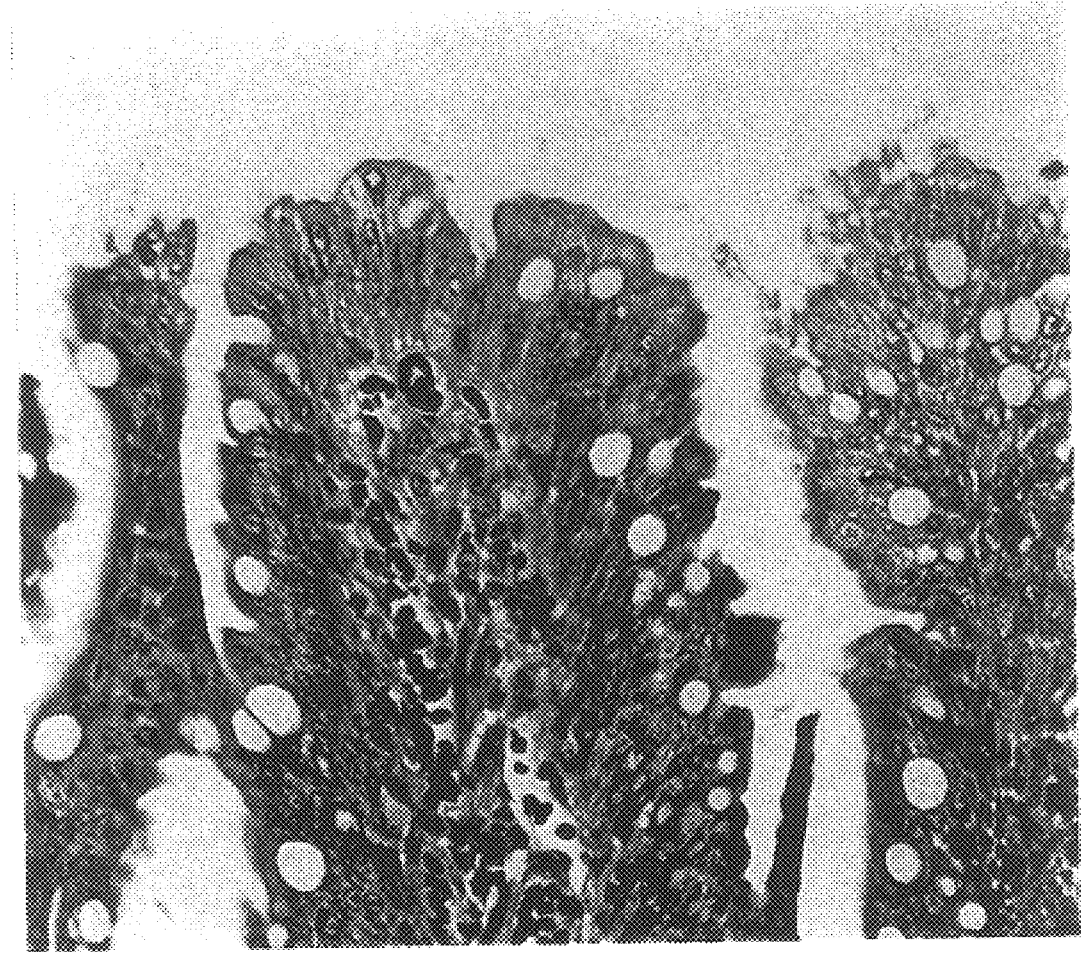
FIG. 4 is a microscopic photograph of a section of duodenal villous tissue taken from a rat of the control group in Test Example 2, the tissue section having been subjected to HE staining (magnification: ×200).
Figure 5:
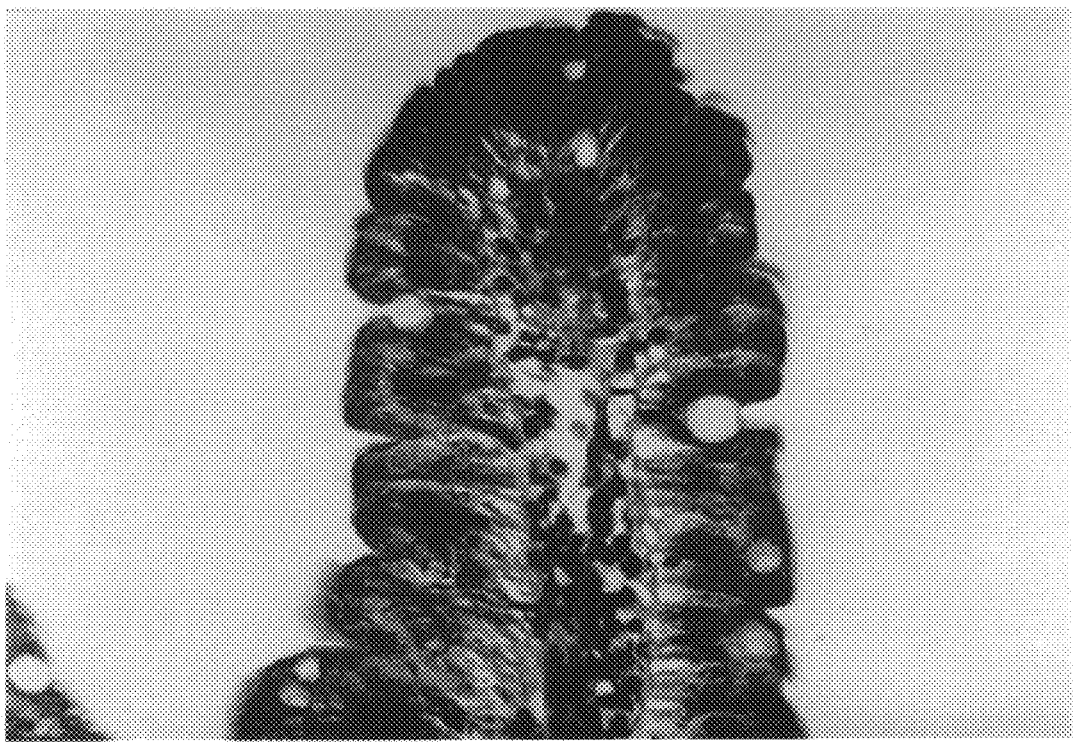
FIG. 5 is a microscopic photograph of a section of duodenal villous tissue taken from a rat of the ethanolamine hydrochloride administration group in Test Example 2, the tissue section having been subjected to HE staining (magnification: ×200).

The results are shown in FIGS. 4 and 5.

In the rats of the control group, necrosis of the villous epithelium and considerable cellular infiltration were observed. In contrast, in the rats of the ethanolamine administration group, necrosis of the villous epithelium was remarkably suppressed and only slight cellular infiltration was observed.

Industrial Applicability

The drug of the present invention for preventing and treating intestinal mucosal disorders prevents atrophy of the intestinal mucosa caused by a long-term administration of pervenous or enteral nutrition. In addition, employment of the drug can prevent lowering of intestinal absorption and diarrhea induced by atrophy; weakening of barrier functions and the intestinal tract immune system; and food allergies. The drug is also effective in the regulation of intestinal flora.

What is claimed is:

1. A method for treating an intestinal mucosal disorder, which comprises administering to a patient in need thereof an effective amount of a member selected from the group consisting of ethanolamine, phosphoethanolamine, phosphoglycerolethanolamine, and salts thereof.

2. The method according to claim 1, wherein the intestinal mucosal disorder is caused by total parental nutrition.

3. The method according to claim 1, wherein the intestinal mucosal disorder is destruction of proliferative crypt cell decreased villous height, or ulceration and necrosis of the gut epithelium.

4. The method of claim 1, wherein the intestinal mucosal disorder is atrophy of the intestinal mucosa.

5. A method for treating a pathological condition caused by an intestinal mucosal disorder, which comprises administering to a patient in need thereof an effective amount of a member selected from the group consisting of ethanolamine, phosphoethanolamine, phosphoglycerolethanolamine, and salts thereof.

6. The method according to claim 5, wherein the pathological condition caused by an intestinal mucosal disorder is bacterial translocation, endotoxic translocation, diarrhea or food allergy.

7. The method according to claim 1, wherein the treatment of intestinal mucosal disorder is made by the reproduction of intestinal mucous cells.

8. The method according to claim 2, wherein the treatment of intestinal mucosal disorder is made by the reproduction of intestinal mucous cells.

9. The method according to claim 3, wherein the treatment of intestinal mucosal disorder is made by the reproduction of intestinal mucous cells.

10. The method according to claim 4, wherein the treatment of intestinal mucosal disorder is made by the reproduction of intestinal mucous cells.

11. The method according to claim 5, wherein the treatment of intestinal mucosal disorder is made by the reproduction of intestinal mucous cells.

12. The method according to claim 6, wherein the treatment of intestinal mucosal disorder is made by the reproduction of intestinal mucous cells.

* * * * *